United States Patent [19]

Lee et al.

[11] Patent Number: 4,781,924
[45] Date of Patent: Nov. 1, 1988

[54] TRANSDERMAL DRUG DELIVERY DEVICE

[75] Inventors: Eun S. Lee, Redwood City; Su I. Yum, Los Altos, both of Calif.

[73] Assignee: ALZA Corporation, Palo Alto, Calif.

[21] Appl. No.: 118,577

[22] Filed: Nov. 9, 1987

[51] Int. Cl.[4] ............................................. A61F 13/00
[52] U.S. Cl. ..................................... 424/449; 414/456
[58] Field of Search ................................. 424/449, 486

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,870,593 | 3/1975 | Elton et al. | 161/159 |
| 3,923,939 | 12/1975 | Baker et al. | 264/49 |
| 4,012,221 | 3/1977 | Walker et al. | 71/66 |
| 4,144,317 | 3/1979 | Higuchi et al. | 424/21 |
| 4,166,111 | 8/1979 | Cardarelli | 424/78 |
| 4,177,256 | 12/1979 | Michaels et al. | 424/22 |
| 4,286,592 | 9/1981 | Chandrasekaran | 128/260 |
| 4,314,557 | 2/1982 | Chandrasekaran | 128/260 |
| 4,379,454 | 4/1983 | Campbell et al. | 604/897 |
| 4,568,343 | 2/1986 | Leeper et al. | 604/896 |
| 4,597,961 | 7/1986 | Etscorn | 424/28 |
| 4,655,766 | 4/1987 | Theeuwes et al. | 604/896 |
| 4,661,105 | 4/1987 | Gale | 604/897 |

FOREIGN PATENT DOCUMENTS 0197504 10/1986 European Pat. Off. .
3438284 3/1985 Fed. Rep. of Germany .

OTHER PUBLICATIONS

Narkis et al., "Slow Release of Water-Soluble Salts from Polymers"; Journal of Applied Polymer Science, vol. 20, pp. 3431-3436, (1976).
Ebert et al., "Development of a Novel Transdermal System Design", Abstract from the Third International Symposium on Recent Advances in Drug Delivery Systems, Feb. 24-29, 1987, Salt Lake City, Utah.

Primary Examiner—Thurman K. Page
Assistant Examiner—L. R. Horne
Attorney, Agent, or Firm—Edward L. Mandell; Shelley G. Precivale; Steven F. Stone

[57] ABSTRACT

A diffusional drug delivery device is described which can provide for stability of the adhesive and system components, elimination of the initial burst of drug and hence irritation, and to provide for delayed onset of therapeutic effect along with delivery of a therapeutic agent at an optimum rate. The therapeutic agent in a first form which is suitable for storage, and the anhydrous activating means are inert when in an anhydrous environment. Moisture activates the system whereby the activating means provides an acidic or basic solution and the first form of the therapeutic agent is converted to a second form which is suitable for absorption through the skin or mucosa.

22 Claims, 3 Drawing Sheets

TRANSDERMAL DRUG DELIVERY DEVICE

FIELD OF THE INVENTION

This invention relates to the transdermal delivery of drugs or other biologically active agents and particularly to novel methods and compositions for providing stable systems under storage conditions. Still more particularly, this invention relates to novel methods and compositions for delaying the onset of drug delivery for transdermal systems.

RELATED PATENT APPLICATIONS

This application is related to the copending, coassigned patent application Ser. No. 07/022,301, filed Mar. 5, 1987 entitled "Moisture Activation of Transdermal Drug Delivery System", which in turn is a continuation of patent application Ser. No. 06/874,263, filed June 13, 1986, of the same title; and to the copending coassigned patent application, Attorney Docket No. 1543 entitled "Improved Transdermal Drug Delivery Device".

BACKGROUND OF THE INVENTION

The transdermal route of parenteral delivery of drugs provides many advantages and transdermal systems for delivering a wide variety of drugs or other beneficial agents are described in U.S. Pat. Nos. 3,598,122, 3,598,123, 4,286,592, 4,314,557, 4,379,454 and 4,568,343 for example, all of which are incorporated herein by reference.

In these devices, a drug or other active agent is released by diffusion from a reservoir through the agent releasing surface of the device to the biological environment at which the device is applied. Such devices perform well in the administration of many agents but are not suitable for the administration of an agent whose dosage regime requires that the onset of therapeutic effect be delayed for a significant period of time after application of the device at the site of delivery. This is because the concentration of the therapeutic agent at the surface through which the agent is released, at the time of application, is typically at or above saturation and is capable of delivering at a rate that can give rise to therapeutic blood levels. In some cases, the initial rate of release is unacceptably high and a method for reducing this initial "burst" of agent delivery is described in U.S. Pat. No. 3,923,939 to Baker et al. Even in this patent, the agent releasing surface of the diffusional embodiment does contain agent and delivery commences immediately in the manner described above.

Non-diffusional devices are known which do not immediately present drug to the biological environment when installed, such as devices which contain material in breakable microcapsules, or fluid imbibing pumps, such as that described in U.S. Pat. No. 4,655,766 of Theeuwes et al. Diffusional delivery devices known to the art however, do not possess this capability.

The devices of this invention are particularly useful in providing a predetermined delayed onset of therapeutic effect for any desired time period after application to the skin. Thus a device could be removed and a new one applied simultaneously, wherein the desired drug-free interval is obtained.

One of the advantages of a continuous release dosage form, such as a transdermal drug delivery device, is the improvement in patient compliance that is obtained from the concurrent removal of one device and application of a new device at the same time. This advantage is lost when removal and application occur at different times or where onset of a therapeutic effect is desired at an inconvenient time such as shortly prior to arousal from sleep. It is not possible, using concurrent application and removal of diffusional delivery devices known in the art, to substantially delay the onset of transdermal drug delivery from the time of application, such as bedtime, until shortly prior to arousal.

Additionally, a common problem encountered with state of the art systems is how to deal with unstable active agents, especially those that tend to degrade the adhesive and other system components. Therefore, there is a continuing need for a transdermal therapeutic system that provides stability of the adhesive and all components during storage.

SUMMARY OF THE INVENTION

An object of this invention is to provide a diffusional drug delivery device which provides for delayed onset of drug administration.

A further object of this invention is to provide a diffusional drug delivery device which does not deliver an initial burst of drug and hence is less likely to cause irritation.

Another object of this invention is to stabilize an active drug by storing it within a transdermal therapeutic system, in form suitable for storage.

A further object of this invention is to provide a diffusional delivery device where the adhesive and other components are protected from degradation by using a drug which in a first form is suitable for storage, said from being more compatible with the system components upon prolonged exposure.

A further object of this invention is to provide for the maintenance of drug potency and device efficacy during prolonged storage periods, whereby the device is inactive while stored, and active when applied to the skin.

A still further object of this invention is to provide a diffusional delivery device which continuously releases drug into a biological environment after a period of no drug delivery.

These and other objects, features, and advantages have been demonstrated by the present invention wherein a controlled release medical device for the delivery of at least one therapeutic agent in a pre-determined delivery rate pattern to a biological environment is comprised of, in combination: reservoir means containing a therapeutic agent which in a first form is suitable for storage and which in a second form is suitable for absorption through the skin or mucosa by reaction with a solution formed by an activating agent and moisture available from the body, the reservoir means having a surface substantially impermeable to therapeutic agent in its first form and permeable to therapeutic agent in its second form, through which the second skin absorbable form of therapeutic agent is released to the biological environment; and activating means containing an activating agent wherein said activating agent in a first state is anhydrous and in a second state is in solution with moisture supplied by the body; whereby the therapeutic agent is changed from its first to its second form by the activating means in its second state and whereby the passage of therapeutic agent to the biological environment by diffusion is impeded until the agent changes forms.

BRIEF DESCRIPTION OF THE DRAWING

In the drawings, which are not drawn to scale, but rather are set forth to illustrate the various embodiments of the invention and wherein like reference numerals designate like parts, the drawings are as follows.

DESCRIPTION OF THE PREFERRED EMBODIMENT

Figure 1:
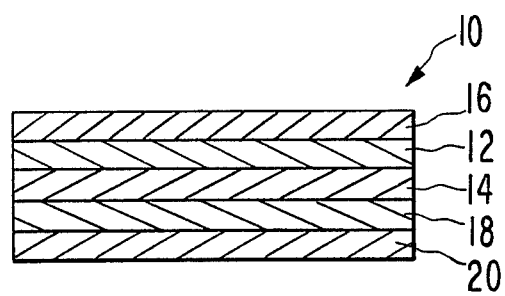
FIGS. 1, 2 and 3 are schematic cross-sectional views of embodiments of the transdermal drug delivery system of this invention, where the drug in a storage suitable form and the activating agent in its first state are in separate reservoirs.

Therapeutic agents suitable for transdermal administration exist in various forms, some of which are more suitable for storage and some of which are more suitable for administration through skin or mucosa. For example, a therapeutic agent may exist in a free base form, a free acid form, a salt form, an ester form, a non-covalent complex or an ionic complex, as for example, agents may exist as the phosphates or glycinates as ion pairs.

Many therapeutic agents such as fluorouracil, barbitol, furosemide, albuterol, apomorphine, benzocaine, acetylsalicylic acid, scopolamine, clonidine, phenylpropanolamine, chlorpheniramine, pilocarpine and ephedrine, for example, are extremely stable in the salt form, such as the sodium, calcium and magnesium cation salts, and the hydrobromide, hydrochloride, maleate, nitrate and sulfate anion salts. These agents, however, may be readily absorbable through the skin only in either the free base form, the free acid form or the ester form, for example. In the past, therefore, transdermal delivery devices storing the agent in the form suitable for absorption through the skin could have an undesirably short storage life. Similarly those storing the agent in a form suitable for storage could have an undesirable low agent delivery rate through skin.

According to this invention, a therapeutic agent delivery device is provided in which the therapeutic agent is converted from the storage suitable form to the delivery suitable or absorbable form after the device is placed into its environment of use in contact with the skin or mucosa as a result of moisture entering the device form the environment of use.

Along with stabilizing an otherwise active compound (drug) by storing it within the system in a stable form suitable for storage, for example in its salt form, this invention has the advantage of protecting the adhesive and other system components from any adverse reactions that are likely to occur upon prolonged exposure to the active drug, as would be the case under storage conditions.

An additional advantage of the transdermal drug delivery system of this invention is the delayed drug delivery and control of the initial excess burst of drug. In this manner, a means for delayed onset is provided which gives a drug-free period in plasma during continuous application of a transdermal drug delivery system.

With reference to the Figures, the devices shown, represent for purposes of illustration, transdermal delivery devices because these are the preferred embodiments of this invention. It must be recognized however, that this invention is applicable to delivery devices generally and in non-transdermal applications, certain components such as the adhesive and backing layers can be omitted. A transdermal delivery device according to this invention may include an impermeable backing member, a therapeutic agent reservoir containing a first storage suitable form of the therapeutic agent which is subsequently converted to a second deliverable form which is suitable for absorption through the skin or mucosa, and an anhydrous activating means which contains an acid or a base activating agent which forms a solution with moisture available from the body and converts the first storage suitable form of the drug to the second deliverable form.

It is believed that this invention has utility in connection with the delivery of drugs within the broad class normally delivered through body surfaces and membranes, including skin and mucosa. As used herein, the expressions "drug" and "therapeutic agent" are used interchangeably and are intended to have their broadest interpretation as any therapeutically active substance which is delivered to a living organism to poduce a desired, usually beneficial, effect. In general, this includes therapeutic agents in all of the major therapeutic areas including, but not limited to those disclosed in U.S. Pat. Nos. 3,598,122, 3,598,123, 4,286,592, 4,314,557, 4,379,454 and 4,568,343, all of which are incorporated herein by reference.

This invention has particular utility in connection with the delivery of all sympathomimetic drugs (bronchodilators) including but not limited to terbutaline, salbutamol and ephedrine. These drugs are placed in a system according to this invention in a storage suitable, preferably salt form, such as terbutaline sulfate, salbutamol sulfate and ephedrine hydrochloride, respectively. Additionally, this invention is useful in delivering ergot alkaloids such as ergonovine and ergotamine, present in a storage suitable form as a salt such as ergonovine mesylate and ergotamine tartrate. Both the sympathomimetrics and the ergot alkaloids in their active forms, have a tendency to be unstable and so this invention is particularly suitable since it uses a storage suitable form of the drug such as a salt, thereby providing a stable system.

This invention also finds utility in connection with the delivery of drugs such as benztropine, nicotine and secoverine. These drugs in their active form, tend to degrade the components of the system, including the adhesive, upon prolonged exposure such as is the case under storage conditions. The storage suitable forms, in particular the salt forms, of these drugs however, do not adversely affect the system's components. Therefore, benztropine mesylate, nicotine tartrate and secoverine hydrochloride can be placed in the system of this invention, to provide delivery of their respective drugs.

As stated above, this invention also eliminates the initial burst of drug. This is particularly beneficial in delivering drugs that have a tendency in large doses, to irritate the skin. These drugs include benztropine, secoverine and nicotine, as noted above, along with beta-blockers such as propranolol and timolol. Storage suitable forms of the latter two drugs are the salt forms propranolol hydrochloride and timolol hydrochloride, respectively.

A diffusional delivery device, in its broadest sense, comprises at least one reservoir means from which at least one therapeutic agent or drug passes by diffusion to the agent releasing surface of the device and from there into the biological environment to which it is applied.

In the preferred embodiment of this invention, a therapeutic agent is transdermally administered to the skin or mucosa, said agent being stored in the diffusional delivery device in a first form suitable for storage, hereinafter referred to as the storage suitable form. Preferably, a salt form of an acid or a base drug is used. Typical examples include, without limitation, nicotine salt, secoverine salt and benztropine salt. The therapeutic agent is converted during delivery from its reservoir, into a second form which is suitable for absorption through skin or mucosa, by reacting with the activating agent which is in solution with moisture supplied by the body, said second form hereinafter referred to as the deliverable form. While the therapeutic agent in its deliverable form is able to permeate the layers of the system and ultimately the skin itself, the storage suitable form of the therapeutic agent can not. The inability of the therapeutic agent in its first form to permeate the system and the skin ensures that the therapeutic agent will remain within the reservoir until the onset of delivery is desired, at which time an activating means converts the therapeutic agent to its deliverable form. Typically, the second or deliverable form of the therapeutic agent is a free base form or a free acid form.

In order that premature reaction be prevented, the therapeutic agent and the activating agent are maintained in an anhydrous environment prior to use. Within these broad limitations, the specific structure of the administration device is not critical to this invention. The therapeutic agent and the activating agent may be dispersed within an anhydrous matrix, either as a solid, non-aqueous liquid or gel, or mixed with suitable anhydrous carriers, permeation enhancers and the like as is known in the art. The devices are preferably in the form of an adhesive patch or the like but can also be in the form suitable for application to the skin or mucosa such as anhydrous ointment, gel or matrix, for example. If desired, means for controlling the release rate can also be used, as is known in the art.

The delivery system of this invention can be used to provide delayed delivery of more than one drug, if desired. If the drugs to be delivered have the same storage suitable form, for example, either the salt of a base drug or the salt of an acid drug, both drugs remain within the reservoir until the onset of delivery is desired, at which time they are converted to their deliverable form by the activating means. Since these deliverable forms are suitable for absorption through skin, the drugs are co-delivered.

This invention can also be used to provide a system where a first drug is continuously delivered, said delivery commencing immediately upon placement of the system on skin, and a second drug is delivered after a predetermined delay. This can be accomplished by utilizing a first drug which is a neutral or nonsalt formable drug such as hydrocortisone, capable of permeating the layers of the system. The second drug is in the storage suitable form, for example, the salt form of an acid or base drug which can not permeate the layers in that form. Moisture from the skin activates the activating means which converts the second drug from its storage suitable form to its deliverable form. This conversion process creates the delay between application of the system and onset of delivery of the second drug.

Alternately, this invention can provide a system that will deliver a first drug and subsequently a second drug, and delivery of the first drug ceases when delivery of the second drug commences. The first drug can be the free form of an acid drug and the second, the salt form of a base drug. Alternately, the first drug can be the free form of a base drug and the second, the salt form of an acid drug. In either case, the system is permeable to the passage of drug in its free form and substantially impermeable to passage of drug in its salt form. When the system is placed upon the skin, delivery of the free form of the drug commences. Meanwhile, moisture available from the body diffuses into the activating means, converting the activating agent to its second state and the activating agent now in solution migrates into the drug reservoir, converting the salt form of the second drug into its free form and likewise converting the free form of the first drug into its salt form. Thus, delivery of the second drug, now in its free form, commences and since the first drug is now in its salt form and therefore impermeable, its delivery ceases.

Figure 2:
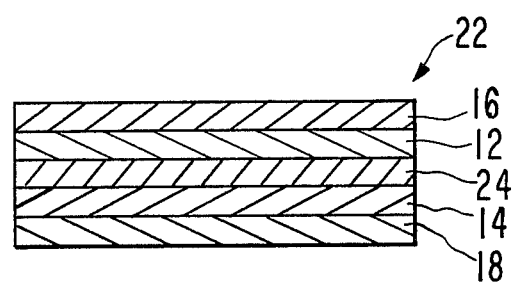
Figure 3:
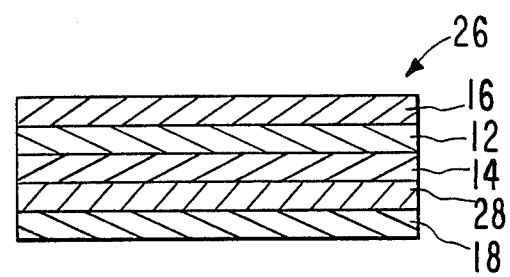

This invention can provide delayed delivery in a variety of embodiments, which are best described with relation to the Figures. FIGS. 1, 2, and 3 illustrate embodiments of the invention which have the reservoir means separate from the activating means. The simplest of these is shown in FIG. 1. System 10 is comprised of drug reservoir means 12 and activating means 14. The system is also provided with an impermeable backing layer 16, an in-line pharmaceutically acceptable contact adhesive 18 and a strippable release liner 20, which is removed prior to application to the skin. The various layers are laminated or otherwise assembled into a bandage having a predetermined size and shape as is known to the art.

The drug reservoir 12 is in the form of a matrix or carrier having a storage suitable form of the drug to be delivered, dispersed throughout. The system components are substantially impermeable to the passage of the storage suitable form of the drug but permeable to the second form of the drug, which is suitable for absorption through the skin or mucosa.

Activating means 14 is a layer comprised of an anhydrous activating agent which can be either an acid or a base dispersed in a matrix or carrier. Suitable acids include without limitation, citric acid, succinic acid, oxalic acid, succinic anhydride, phthalic acid, phthalic anhydride, sodium bisulfate and salicylic acid. Likewise, suitable bases include without limitation, $Na_2CO_3$, $NaHCO_3$, $K_2CO_3$, $KHCO_3$, $Na_3PO_4$, $Na_2HPO_4$, sodium oxalate, sodium succinate, sodium citrate, sodium salicylate, and all other salts of organic acids.

When the system 10 is first placed on the patient's skin, the system- or skin-impermeable storage suitable form of the drug in reservoir 12 is sequestrated from the activating means 14 and reservoir 12 is substantially free of activating agent. Likewise, the activating means 14 is substantially free of drug, both the storage suitable and the deliverable form. This is due to the fact that in an anhydrous environment such as is the case at storage conditions, the drug in its first form, in reservoir 12 and the activating agent in activating means 14 are for the most part, non-reactive.

In accordance with a preferred embodiment of the invention, the activating means 14 is activated by moisture, which is readily available from the site of administration such as the cutaneous surface, particularly in occluded regions. Means 14 may alternatively be moistened by dipping into a liquid containing vessel immediately prior to application. In operation, this moisture migrates into the system 10 from the skin surface or other source, typically by osmosis or diffusion, passing through the adhesive layer 18 and then to the activating means 14 where it mixes with the acid or base contained therein. The acid or base forms an acidic or basic solution and migrates into the salt drug layer, reacting with the salt drug to convert it into its free form which then passes freely through layers 14 and 18 and then through the skin.

The drug releasing surfaces of certain embodiments of our invention are characterized by being substantially free of drug at the time they are applied to the body. As used herein, the expression "substantially free of drug" means either free of drug or containing an amount of drug insufficient to establish untoward effects on skin (eg. irritation) or to establish and maintain therapeutically effective drug delivery rates at the time of application to the delivery site. In this manner, the adhesive layer 18 is substantially free of drug.

FIG. 2 illustrates another embodiment of the invention where the laminated system 22 is provided with a rate controlling membrane 24 positioned between the drug reservoir 12 and the activating means 14. Membrane 24 controls the rate at which activating agent diffuses from means 14 into reservoir 12. Therefore, the rate at which the storage suitable form of the drug is converted and subsequently delivered, is also controlled, indirectly.

Membrane 24 is fabricated of a material such that it is substantially impermeable to the passage of the first form of the drug and to the contents of layer 12, and substantially permeable to the passage of the activating agent in solution with water or other biological fluid, and also permeable to drug in its second form. This rate controlling membrane may be fabricated from permeable, semipermeable or microporous materials which are known in the art to control the rate of agents and/or fluids into and out of delivery devices. It is preferable that the in vitro flux of agent in solution across membrane 24 is less than the rate (per cm$^2$) that said agent goes into solution. However, this invention also contemplates use of a membrane having an in vitro flux greater than or equal to that rare that agent goes into solution.

FIG. 3 illustrates an embodiment similar in construction to that of FIG. 2. Laminated system 26 also has a rate controlling membrane 28. However, in system 26, the membrane 28 is interposed between the activating means 14 and the adhesive 18. In this embodiment, the membrane 28 controls the rate at which moisture enters the system, and therefore the rate at which the activating means 14 becomes hydrated.

Membrane 28 is fabricated from a material such that it is substantially impermeable to the passage of the activating agent and other components of activating means 14, and substantially permeable to the passage of drug in its second form. The membrane is preferably of a material such that the in vitro flux of moisture across membrane 28 is less than the in vitro flux of moisture through the skin.

Figure 4:
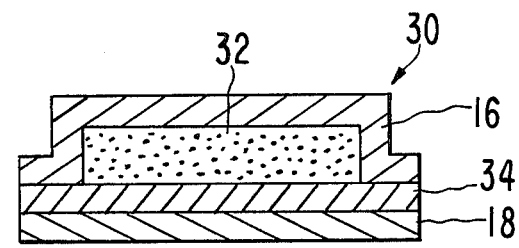
FIGS. 4, 5 and 6 are schematic cross-sectional views of embodiments of the transdermal drug delivery system of this invention, where the drug in a storage suitable form and the activating agent in its first state are in the same reservoir.
Figure 5:
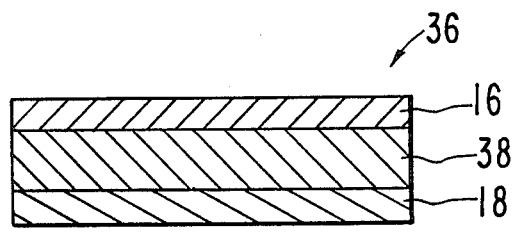
Figure 6:
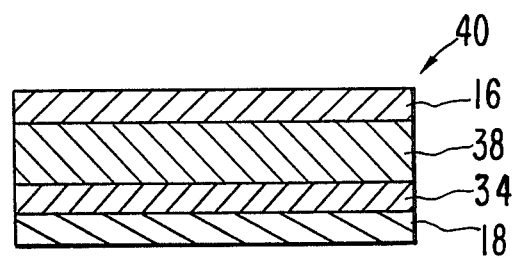

FIGS. 4, 5 and 6 illustrate embodiments of the invention where the drug reservoir and the activating means are combined, i.e. there is a single reservoir containing both the drug in its storage suitable form and the activating agent.

In FIG. 4, system 30 is comprised of a reservoir 32 and a rate controlling membrane 34. Membrane 34 controls the rate at which moisture enters reservoir 32. The reservoir 32 is formed by dry blending the drug in its first form, and an activating agent, without any carrier vehicle or nonaqueous vehicle. The first form of the drug can not permeate membrane 34 until moisture is available from the skin or other source. When moisture becomes available, it passes through membrane 34 and into the reservoir 32 where the activating agent becomes hydrated and converts the first form to the second form of the drug, which then can pass through membrane 34 and adhesive 18. Backing member 16, instead of being flat, forms an envelope or pouch in which the reservoir 32 is held. This configuration is especially suitable for use when the reservoir 32 is not self-supporting.

FIG. 5 illustrates a laminated system 36 having a single reservoir 38 where the drug in its first form and the activating agent are dispersed throughout a matrix or carrier. In FIG. 6, laminated system 40 has a rate controlling membrane 34 positioned between the drug-/agent reservoir 38 and the adhesive 18.

Figure 7:
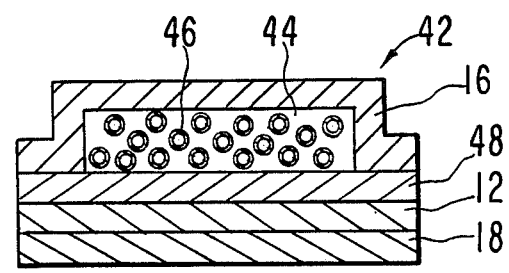
FIG. 7 is a schematic cross-sectional view of an embodiment of the transdermal drug delivery system of this invention where the activating agent in its second state is microencapsulated.

The embodiments of FIGS. 1-6 rely on external moisture to activate the system, whereby moisture from the skin forms an aqueous solution with the activating agent which can then convert the drug from its first storage suitable form into its second deliverable form. FIG. 7 provides a system where the activating agent in an aqueous solution is actually placed into the system 42, thereby avoiding the need for an external source of moisture.

System 42 is comprised of an agent reservoir 44 where an aqueous solution of activating agent is microencapsulated in wax. These microcapsules 46 can be broken and the solution released upon application of pressure or they can be melted and the solution released upon application of heat. The activating solution then migrates through the microporous membrane 48 and into the drug reservoir 12 where the drug in its first form is converted to the second absorbable form of the drug, which is then delivered to the skin.

Microporous membrane 48 may be formed from polymers such as polypropylene, polytetrafluorethylene, polycarbonates, polyvinylchloride, cellulose acetate, cellulose nitrate and polyacrylonitrile, for example.

Figure 8:
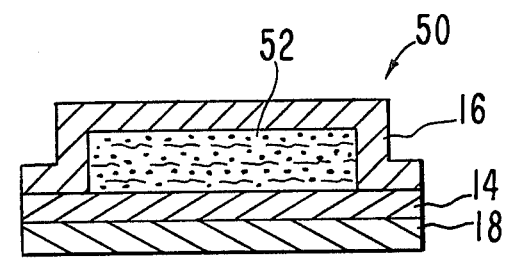
FIGS. 8 and 9 are schematic cross-sectional views of embodiments of the transdermal drug delivery system of this invention, where the drug in its first state is in a non-aqueous medium.
Figure 9:
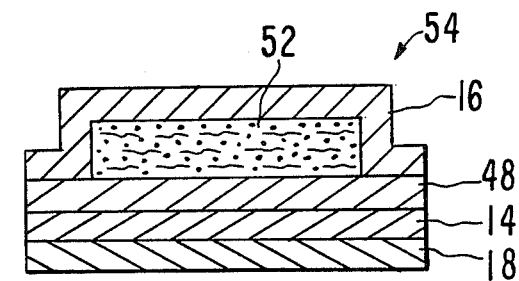

The embodiments of FIGS. 8 and 9 illustrate placement of the storage suitable form of the drug in a nonaqueous medium as compared to a polymeric matrix. Suitable materials for the nonaqueous medium include, without limitation, mineral oil, silicone oil and petrolatum.

FIG. 8 shows system 50 having the drug/non-aqueous medium in reservoir 52. The system 54 of FIG. 9 has the same reservoir but additionally has a microporous membrane 48 interposed between reservoir 52 and the activating agent reservoir 14.

Figure 10:
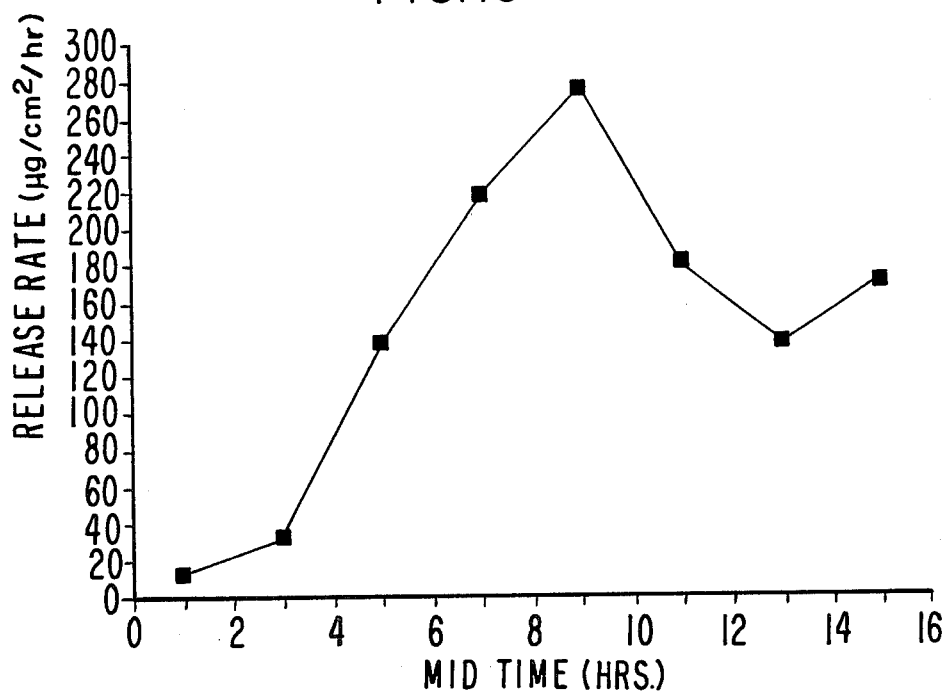
FIGS. 10 and 11 are graphs illustrating the release rate of nicotine from transdermal drug delivery systems according to this invention.

FIG. 10 is a graphical representation of the theoretical release rate profile versus time for the system illustrated in FIG. 3. The system 26 would be positioned on the skin at time zero. From time zero until time t, moisture from the skin would diffuse through the rate controlling membrane 28, into the activating layer 14 and acid or base in solution would migrate into the drug layer 12 to convert the drug in its first form to its second absorbable form, which subsequently would diffuse through the layers to reach the skin surface. Shortly after time t, the drug would begin to actually be delivered into the bloodstream. This is indicated by the rise on the curve in FIG. 10.

The delay time (time zero until time t) depends upon both the water migration through the rate controlling membrane 28 and the activating layer 14.

Various materials suited for the fabrication of the various layers are disclosed in the aforementioned patents. The polymer matrix of the drug reservoir 12, the activating agent reservoir 14, and combined reservoir 38, are anhydrous and suitable materials include without limitation, natural and synthetic rubbers or other polymeric materials, thickened mineral oil or petroleum jelly. The preferred embodiment according to this invention is fabricated from an ethylene/vinylacetate (EVA) copolymer of the type described in U.S. Pat. No. 4,144,317, preferably those having a vinylacetate content in the range of about 18 to 60 weight percent. Particularly good results have been obtained using an EVA copolymer of about 40 weight percent vinylacetate content (40 w % VA). The drug and/or agent is preferably dispersed through the matrix at a concentration in excess of saturation, the amount of the excess being a function of the intended useful life of the system.

In addition to the drug and/or agent, the matrix may also contain other materials such as dyes, pigments, inert fillers, permeation enhancers, excipients and conventional components of pharmaceutical products or transdermal therapeutic systems as is known to the art. The drug and/or the activating agent containing matrices may also contain a salt such as NaCl, which facilitates the onset of drug delivery by osmotically drawing up moisture from the skin.

One face surface of the drug reservoir bears a backing member 16. The purpose of the backing is to prevent passage of the drug through the surface of the reservoir distant from the adhesive layer. An ancillary purpose of the backing is to provide support for the system, where needed. The backing layer can be flexible or nonflexible and suitable materials include without limitation, cellophane, cellulose acetate, ethylcellulose, plasticized vinylacetate-vinylchloride copolymers, polyethylene terephthalate, nylon, polyethylene, polypropylene, metalized polyester films, polyvinylidene chloride, coated flexible fibrous backings such as paper and cloth and aluminum foil. Such backings can be in the form of precast films or fabrics which are bonded to the reservoir by heat or adhesives and can be coated onto the reservoir. Numerous other suitable materials are disclosed in U.S. Pat. No. 4,661,105, incorporated herein by reference.

The composition and thickness of adhesive layer 18 are such that layer 18 does not constitute a significant permeation barrier to the passage of drug. Adhesive layer 18 may also contain a predetermined amount of the skin absorbable form of the drug which serves to saturate the skin for more rapid therapeutic effects where desired. Silicone compounds are commonly used as adhesives, however numerous materials are known which possess the requisite strength and skin compatibility. An adhesive overlay or other means for maintaining the device on the skin can be employed instead of, or in combination with, adhesive lamina 18. Suitable adhesive materials are noted in the aforementioned patent.

In operation, liner 20 is removed and the system is placed in direct contact with the skin. The releaseable liner is made from materials which are substantially impermeable to the drug, and any other components of the layers. The same materials that are used to make the backing layer may be used to make the liner, provided they are made strippable such as by siliconizing.

The aforementioned patents describe a wide variety of materials which can be used for fabricating the various layers of the transdermal delivery systems according to this invention. This invention therefore contemplates the use of materials other than those specifically disclosed herein, including those which may hereafter become known to the art to be capable of performing the necessary functions.

EXAMPLE I

A test sample was designed to deliver nicotine according to this invention. Nicotine which is transdermally administered to facilitate breaking the tobacco habit, is especially suited to illustrate this invention. Nicotine in its active form tends to degrade adhesives, especially those which are silicone based. Also, nicotine delivered in a sudden burst may irritate the skin. Therefore, use of this invention to deliver nicotine provides a system with an improved shelf-life by storing the nicotine in its salt form, and further provides elimination of the initial burst of drug by storing nicotine in a form which is not readily absorbed through mucous membrane and intact skin.

The drug reservoir was a polymeric matrix comprised of 60% nicotine tartrate and 40% EVA 40 carrier, and was about 6.5 mils thick. The activating layer was about 3.5 mils thick and was a polymeric matrix comprised of 60% $Na_2CO_3$ and 40% EVA 40 carrier. Sodium carbonate provides an aqueous solution which is strongly alkaline. Thus, in this particular embodiment, the activating layer was a base.

The release rate was measured at 35° C. using a 1.5 mil Hytrel ® (Du Pont) membrane, which simulates water diffusion through human skin. The release rate profile is illustrated in FIG. 10.

Prior to application to the Hytrel ® membrane, the activating layer is anhydrous and therefore inert and is substantially impermeable to the passage of drug and is thus substantially free of drug, both nicotine and nicotine tartrate. When the system is placed in contact with the Hytrel ® membrane, moisture migrates through the membrane and into the activating layer which then becomes hydrated and active.

Moisture entering the EVA polymeric matrix reacts with the solid $Na_2CO_3$ to form a basic solution. Thus, the activating agent undergoes a change of state from a first anhydrous and inert state to a second hydrated and active state, where the activating agent is in solution.

The basic solution then diffuses through the activating matrix and into the drug reservoir, where it reacts with the solid nicotine tartrate to covert it to its free form, nicotine. The agent nicotine then passes freely through the activating layer and then through the Hytrel ® membrane. The activating layer in its dry state is impermeable to the passage of nicotine tartrate but in its hydrated state, is permeable to the passage of nicotine.

EXAMPLE II

A system was designed according to this invention and is illustrated in FIG. 7. The backing was standard Medpar ® and the system had the storage suitable form of the drug and the activating agent (base) mixed in the same reservoir. The drug reservoir was comprised of 42% nicotine tartrate, 18% $Na_2CO_3$ and 40% EVA 40 carrier. The system had a PVA rate controlling membrane about 1.5 mils thick and had a silicone adhesive layer.

The release rate of nicotine from this system at 35° C. in a release medium of water, is presented in the following table:

TABLE I

| Time, hrs | Average Release Rate, $\mu g/cm^2/hr$ |
| --- | --- |
| 2 | 72.64 |
| 4 | 29.55 |
| 6 | 45.84 |
| 8 | 52.60 |
| 13 | 112.51 |

As is evidenced from the data presented, this system provides the desired delayed onset where the drug release rate during the first 8 hours is minimal and gradually increases to a significant level at 13 hours.

EXAMPLE III

A test sample was designed to deliver nicotine. The drug reservoir was a polymeric matrix comprised of 40% nicotine tartrate, 50% EVA 40 carrier and 10% NaCl, and was about 8 mils thick. The activating layer was about 3.5 mils thick and was a polymeric matrix comprised of 60% $Na_2CO_3$ and 40% EVA 40 carrier.

Figure 11:
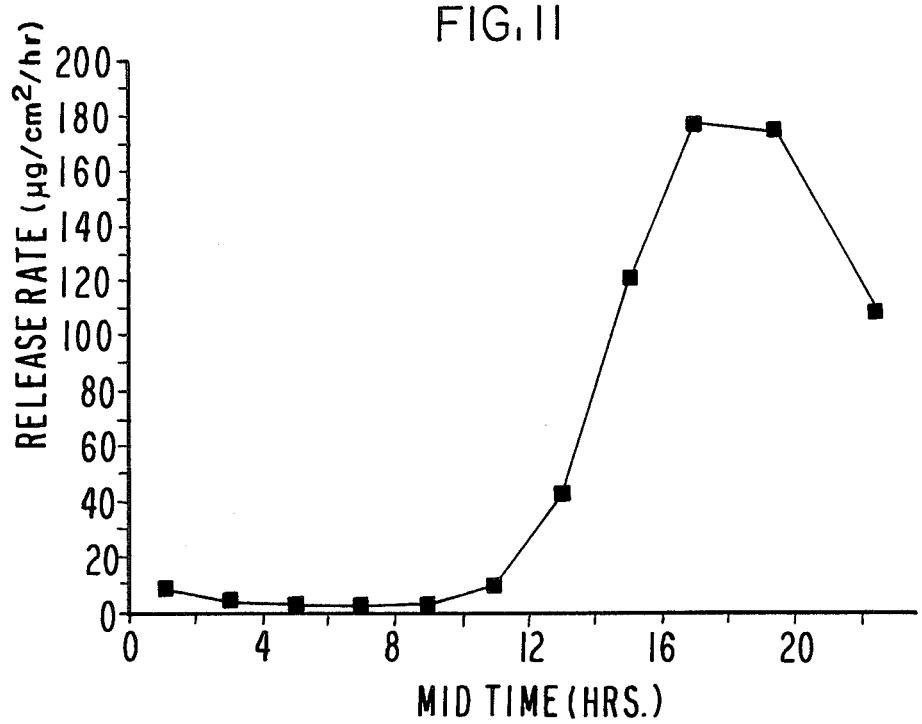

The release rate was measured using a 1.5 mil Hytrel ® membrane and is graphically illustrated in FIG. 11.

Having thus generally described our invention and described in detail certain preferred embodiments thereof, it will be readily apparent that various modifications to the invention may be made by workers skilled in the art without departing from the scope of this invention which is limited only by the following claims.

What is claimed is:

1. A controlled release medical device for delivery of at least one therapeutic agent in a pre-determined delivery rate pattern to a biological environment comprising, in combination:

reservoir means containing a therapeutic agent which in a first form as a salt is suitable for storage and in a second form is a member selected from the group consisting of a free acid, a free base, an ester, is suitable for absorption through the skin or mucosa, and said reservoir means having a surface substantially impermeable to said therapeutic agent in said first form and permeable to said therapeutic agent in said second form and through which the second form of said therapeutic agent is released to the biological environment; and activating means containing an activating agent wherein said activating agent in a first state is anhydrous, and in a second state is hydrated and in solution wherein said means is in the only anhydrous form;

whereby the therapeutic agent is changed from its first to its second form by the activating means in its second state and whereby the passage of therapeutic agent to the biological environment by diffusion is impeded until the therapeutic agent changes form.

2. The device of claim 1 wherein the activating means is moistened by cutaneous liquids, whereby said activating agent is changed from said first to said second state.

3. The device of claim 1 wherein said reservoir means is a matrix having a therapeutic agent dispersed throughout, said means being substantially free of activating agent.

4. The device of claim 3 wherein said activating means is a matrix having an activating agent dispersed throughout, said means being substantially free of therapeutic agent.

5. The device of claim 4 which further comprises:
   rate controlling means for controlling the rate at which said activating means becomes hydrated when placed at its environment of use.

6. The device of claim 4 which further comprises:
   rate controlling means for controlling the rate at which said activating agent in its second state diffuses into said reservoir means.

7. The device of claim 1 wherein said reservoir means and said activating means comprise a single reservoir having a therapeutic agent and activating agent contained therein, in a dry blend.

8. The device of claim 7 which further comprises:
   rate controlling means for controlling the rate at which said activating agent becomes hydrated.

9. The device of claim 1 wherein said reservoir means and said activating means comprise a single reservoir having a therapeutic agent and activating agent contained therein, dispersed throughout a matrix.

10. The device of claim 9 which further comprises:
    rate controlling means for controlling the rate at which said activating agent becomes hydrated.

11. The device of claim 1 wherein said reservoir means is comprised of a therapeutic agent in a non-aqueous medium, said means being substantially free of activating agent.

12. The device of claim 11 wherein said activating means is a matrix having an activating agent dispersed throughout, said means being substantially free of therapeutic agent.

13. The device of claim 12 which further comprises:
    rate controlling means for controlling the rate at which activating agent in its second state diffuses into said reservoir means.

14. The device of claim 1 wherein said reservoir means is comprised of a first and a second therapeutic agent which are codelivered.

15. The device of claim 14 wherein said first and second therapeutic agents in a first form are salt forms of base drugs.

16. The device of claim 14 wherein said first and second therapeutic agents in a first form are salt forms of acid drugs.

17. The device of claim 14 wherein said first therapeutic agent is a non-salt drug and said second therapeutic agent in a first form is a salt form of a drug, and delivery of the second therapeutic agent is delayed until a change of state occurs.

18. The device of claim 1 wherein said reservoir means is comprised of a first and a second therapeutic agent, where delivery of the second therapeutic agent commences when delivery of the first therapeutic agent ceases.

19. The device of claim 18 wherein said first therapeutic agent in a first form is the salt form of an acid drug and said second therapeutic agent is the free form of a base drug.

20. The device of claim 18 wherein said first therapeutic agent in a first form is the salt form of a base drug and said second therapeutic agent is the free form of an acid drug.

21. The device of claim 1 wherein said therapeutic agent is selected from the group consisting of fluorouracil, barbitol, furosemide, albuterol, apomorphine, benzocaine, acetylsalicylic acid, scopolamine, clonidine, phenylpropanolamine, chlorpheniramine, pilocarpine, terbutaline, salbutamol, ephedrine, ergonovine, ergotamine, benztropine, nicotine, secoverine, propranolol and timolol.

22. A controlled release medical device for delivery of nicotine in a pre-determined delivery rate pattern to a biological environment comprising, in combination:
reservoir means containing nicotine tartrate which is a form of nicotine suitable for storage, said nicotine tartrate being subsequently changed to nicotine which is suitable for absorption through the skin or mucosa, and said reservoir means having a surface substantially impermeable to nicotine tartrate and permeable to nicotine and through which nicotine is released to the biological environment; and
activating means containing an activating agent wherein said activating agent in a first state is anhydrous, and in a second state is hydrated and in solution; and said activating means is in the anhydrous form
whereby nicotine tartrate is changed to nicotine by the activating means in its second state and whereby the passage of nicotine to the biological environment by diffusion is impeded until the nicotine tartrate changes form.

* * * * *

UNITED STATES PATENT AND TRADEMARK OFFICE
CERTIFICATE OF CORRECTION

PATENT NO. : 4,781,924

DATED : November 1, 1988

INVENTOR(S) : Eun Soo Lee and Su I. Yum

It is certified that error appears in the above-identified patent and that said Letters Patent is hereby corrected as shown below:

Column 2, Line 34, "from" should be --form--. Column 3, Line 62, "form" should be --from--. Column 7, Line 56, "rare" should be --rate--. Column 11, Line 54 "base, an ester" should be --base and an ester--; Line 65, delete "only".

Signed and Sealed this

Fourth Day of April, 1989

Attest:

DONALD J. QUIGG

Attesting Officer

Commissioner of Patents and Trademarks